(12) United States Patent
Kothrade et al.

(10) Patent No.: US 6,528,089 B1
(45) Date of Patent: Mar. 4, 2003

(54) METHOD FOR PRODUCING SOLID DOSING FORMS

(75) Inventors: Stephan Kothrade, Limburgerhof (DE); Helmut Meffert, Mannheim (DE); Gunther Berndl, Herxheim (DE); Andreas Ernst, Worms (DE); Axel Sanner, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/555,596

(22) PCT Filed: Nov. 30, 1998

(86) PCT No.: PCT/EP98/07716

§ 371 (c)(1),
(2), (4) Date: May 31, 2000

(87) PCT Pub. No.: WO99/27916

PCT Pub. Date: Jun. 10, 1999

(30) Foreign Application Priority Data

Dec. 1, 1997 (DE) .......................................... 197 53 298

(51) Int. Cl.$^7$ ................................................. A61K 9/20
(52) U.S. Cl. ...................... 424/464; 424/474; 424/484; 424/486; 424/489; 514/772.1
(58) Field of Search ................................. 424/484, 464, 424/486, 474, 487, 489, 78.08, 78.24; 514/772.1

(56) References Cited

U.S. PATENT DOCUMENTS

| 4,361,689 A | | 11/1982 | Patel et al. .................. 526/264 |
| 4,693,887 A | | 9/1987 | Shah ............................ 424/19 |
| 4,801,460 A | | 1/1989 | Goertz et al. ................ 424/465 |
| 4,880,585 A | | 11/1989 | Klimesch et al. ........... 264/141 |
| 4,957,681 A | | 9/1990 | Klimesch et al. ........... 264/211 |
| 5,073,379 A | | 12/1991 | Klimesch et al. ........... 424/467 |
| 6,015,213 A | * | 1/2000 | Nakada et al. ............... 351/172 |
| 6,075,107 A | | 6/2000 | Kothrade et al. ........... 526/264 |

FOREIGN PATENT DOCUMENTS

| EP | 240 904 | 10/1987 |
| EP | 240 906 | 10/1987 |
| EP | 337 256 | 10/1989 |
| EP | 358 105 | 3/1990 |
| GB | 1 522 759 | 8/1978 |
| GB | 1 563 390 | 3/1980 |

* cited by examiner

*Primary Examiner*—Thurman K. Page
*Assistant Examiner*—Liliana Di Nola-Baron
(74) *Attorney, Agent, or Firm*—Keil & Weinkauf

(57) ABSTRACT

Solid dosage forms are obtained by mixing at least one polymeric binder, at least one active ingredient, and, where appropriate, conventional additives to form a plastic mixture, and shaping, using as polymeric binder a copolymer of an N-vinyllactam and a copolymerizable monomer having a hydrophobic radical. Dosage forms which show slow release of the active ingredient are obtained in a simple and low-cost manner.

20 Claims, No Drawings

METHOD FOR PRODUCING SOLID DOSING FORMS

The invention relates to a process for producing solid dosage forms by mixing at least one polymeric binder, at least one active ingredient and, where appropriate, conventional additives to form a plastic mixture, and shaping the mixture. The invention particularly relates to a process for producing solid pharmaceutical dosage forms.

Classical processes for producing solid pharmaceutical forms, especially tablets, are carried out batchwise and comprise a plurality of stages. Pharmaceutical granules represent an important intermediate therefor. Thus, for example, it is evident from Bauer, Frömmig and Fuhrer, Pharmazeutische Technologie, Georg-Thieme-Verlag, pages 292 et seq., that drug forms can be obtained from the melt by dry granulation. The possibility of producing solidified melt granules either by melting and shock solidification, by casting and comminuting or by prilling in spray towers is described. One problem with these processes is the accurate shaping which is necessary for producing drugs. Irregular particles or fragments are produced, so that the resulting shape by no means corresponds to customary drug forms, and granules therefore have only little importance as a drug form on their own. Production of desired solid drug forms requires the use of further process steps such as compression in tabletting machines. This is time-consuming and costly. A considerably simpler continuous process for producing solid pharmaceutical forms has been known for some time and entails extruding a solvent-free melt of a polymeric binder containing active ingredients, in shaping the extrudate to the required drug form, for example in a calender with molding rolls, see EP-A-240 904, EP-A-240 906, EP-A-337 256 and EP-A-358 105 (melt extrusion). It is possible in this way to achieve specific shaping. The polymeric binders employed are, in particular, polymers of N-vinylpyrrolidone or copolymers thereof, eg. with vinyl acetate.

Dosage forms based on such polymers have the disadvantage that they release the active ingredient relatively rapidly. It is therefore impossible to produce slow-release dosage forms without taking additional measures, such as applying a coating which controls their release.

It is an object of the present invention to provide dosage forms which can be produced by melt extrusion and are able to release the active ingredient slowly.

We have found that this object is achieved by using as polymeric binder a copolymer of an N-vinyllactam and a copolymerizable monomer having a hydrophobic radical.

The present invention therefore relates to a process for producing solid dosage forms by mixing at least one polymeric binder, at least one active ingredient and, where appropriate, conventional additives to form a plastic mixture, and shaping, wherein the polymeric binder used is a copolymer of an N-vinyllactam of the formula I:

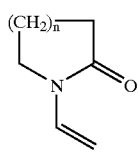
(I)

where n is 1, 2 or 3, and at least one copolymerizable monomer having a hydrophobic radical.

The process according to the invention makes it possible to produce solid dosage forms with slow release (sustained release) of the active ingredient in a simple and low-cost manner.

Dosage forms mean herein all forms which are suitable for use as drugs, plant treatment compositions, human and animal foods and for delivering fragrances and perfume oils. These include, for example, tablets of any shape, pellets, granules, but also larger forms such as cubes, blocks (bricks) or cylindrical forms, which can be used, in particular, as human or animal foods.

The dosage forms obtainable according to the invention generally comprise:

a) 0.1–90% by weight, in particular 0.1–60% by weight (based on the total weight of the dosage form), of an active ingredient, b) 10–99.9% by weight, in particular 40–99.9% by weight, of a polymeric binder and c) where appropriate additives.

The copolymer used as binder comprises as hydrophobic comonomer in particular units of a compound of the formula II:

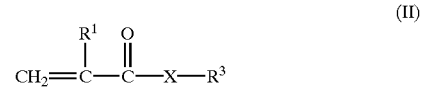
(II)

where $R^1$ is a hydrogen atom or a methyl group, X is O, NH or $NR^2$, $R^2$ is $C_1$–$C_{30}$-alkyl, and $R^3$ is $C_8$–$C_{30}$-alkyl, $C_8$–$C_{30}$-cycloalkyl or $C_8$–$C_{30}$-alkenyl. The comonomer thus comprises (meth)acrylic esters or (meth)acrylamides having a hydrophobic $C_8$–$C_{30}$-alkyl, $C_8$–$C_{30}$-cycloalkyl or $C_8$–$C_{30}$-alkenyl group. $R^2$ is preferably $C_1$–$C_{18}$-alkyl and $R^3$ is $C_8$–$C_{18}$-alkyl or $C_8$–$C_{18}$-alkenyl.

Examples of suitable acrylic and methacrylic esters are octyl acrylate, 2-ethylhexyl acrylate, nonyl acrylate, decyl acrylate, lauryl acrylate, myristyl acrylate, cetyl acrylate, stearyl acrylate, oleyl acrylate, behenyl acrylate, hexyl methacrylate, octyl methacrylate, nonyl methacrylate, decyl methacrylate, lauryl methacrylate, myristyl methacrylate, cetyl methacrylate, stearyl methacrylate, oleyl methacrylate, behenyl methacrylate and tert-butylcyclohexyl acrylate.

Examples of acrylamides and methacrylamides which can be used are N-stearylacrylamide, N-stearylmethacrylamide, N-octylacrylamide, N,N-dioctylacrylamide, N,N-dioctylmethacrylamide, N-cetylacrylamide, N-cetylmethacrylamide, N-dodecylacrylamide, N-dodecylmethacrylamide, N-myristylacrylamide and 2-ethylhexylacrylamide.

Particularly preferred copolymers comprise ethylhexyl, lauryl, myristyl, cetyl, stearyl, oleyl or behenyl acrylate or methacrylate units.

The polymeric binder may also comprise as monomer having a hydrophobic radical a vinyl ester of an aliphatic $C_8$–$C_{30}$-carboxylic acid, in particular a $C_8$–$C_{18}$-carboxylic acid. It is possible to use, for example, the vinyl esters of decanoic acid, lauric acid, myristic acid, palmitic acid, stearic acid, oleic acid and behenic acid.

It is, of course, also possible for the polymeric binder to comprise any desired mixtures of said monomer units.

The polymeric binder contains 50–99 mol %, preferably 70–99 mol %, and particularly preferably 90–99 mol %, of N-vinyllactam units. It contains 1–50 mol %, preferably 1–30 mol %, and in particular 1–10 mol %, of units of monomer having the hydrophobic radical.

In addition, the polymeric binder may contain units of other copolymerizable monomers (other comonomers) in an amount of 0.5 to 48% by weight, preferably 0.5 to 20% by weight, and particularly preferably 0.5 to 10% by weight. Other suitable comonomers are, in particular, monoethylenically unsaturated carboxylic acids having 3 to 8 carbon atoms, such as acrylic acid, methacrylic acid, dimethyl acrylic acid, ethacrylic acid, maleic acid, citraconic acid, methylenemalonic acid, allylacetic acid, vinylacetic acid, croton acid, fumaric acid, mesaconic acid and itaconic acid, and the monoesters of said dicarboxylic acids with $C_1$–$C_{18}$-alkanols. Acrylic acid, methacrylic acid, maleic acid or mixtures of said carboxylic acids are preferred. The monoethylenically unsaturated carboxylic acids can be employed in the form of the free acid and, where available, of the anhydrides or in partially or completely neutralized form. The neutralization is preferably carried out with alkali metal or alkaline earth metal bases, ammonia or amines, e.g. sodium hydroxide, potassium hydroxide, sodium carbonate, potassium carbonate, sodium bicarbonate, magnesium oxide, calcium hydroxide, calcium oxide, gaseous or aqueous ammonia, triethylamine, ethanolamine, diethanolamine, morpholine, diethylenetriamine or tetraethylenepentamine.

Further examples of suitable comonomers are the esters of the abovementioned carboxylic acids with $C_1$–$C_6$-alkanols, $C_1$–$C_4$-diols, mono- and di-$C_1$–$C_4$-alkylamino-$C_1$–$C_4$-alkanols, and the amides, mono- and di-$C_1$–$C_4$-alkylamides and nitriles of these carboxylic acids, e.g. methyl acrylate, ethyl acrylate, methyl methacrylate, ethyl methacrylate, hydroxyethyl acrylate, hydroxypropyl acrylate, hydroxybutyl acrylate, hydroxyethyl methacrylate, hydroxypropyl methacrylate, hydroxyisobutyl acrylate, hydroxyisobutyl methacrylate, monomethyl maleate, dimethyl maleate, monoethyl maleate, diethyl maleate, 2-ethylhexyl acrylate, 2-ethylhexyl methacrylate, acrylamide, methacrylamide, N,N-dimethylacrylamide, N-tert-butylacrylamide, acrylonitrile, methacrylonitrile, dimethylaminoethyl acrylate, diethylaminoethyl acrylate, diethylaminoethyl methacrylate and the salts of the last-mentioned monomers with carboxylic acids or mineral acids or the quaternized products.

Also suitable as copolymerizable monomers are acrylamidoglycolic acid, vinylsulfonic acid, allylsulfonic acid, methallylsulfonic acid, styrenesulfonic acid, 3-sulfopropyl acrylate, 3-sulfopropyl methacrylate and acrylamidomethylpropanesulfonic acid, and phosphono-containing monomers such as vinylphosphonic acid, allylphosphonic acid and acrylamidomethylpropanephosphonic acid.

Further suitable copolymerizable monomers are N-vinylimidazole, N-vinyl-2-methylimidazole, N-vinyl-4-methylimidazole, diallylammonium chloride, vinyl esters such as vinyl acetate and vinyl propionate, and vinylaromatic compounds such as styrene. It is, of course, also possible to employ mixtures of said monomers.

The copolymers are prepared by known processes, e.g. of solution, precipitation, suspension or inverse suspension polymerization, or of emulsion or inverse emulsion polymerization, using compounds which form free radicals under the polymerization conditions.

The polymerizations are normally carried out at from 30 to 200° C., preferably 40 to 110° C. Examples of suitable initiators are azo and peroxy compounds, and the usual redox initiator systems, such as combinations of hydrogen peroxide and reducing compounds, e.g. sodium sulfite, sodium bisulfite, sodium formaldehyde sulfoxylate and hydrazine.

The copolymers have K values of at least 7, preferably 10 to 100, particularly preferably 10 to 50. The K values are determined by the method of H. Fikentscher, Cellulose-Chemie, 13 (1932) 58–64 and 71–74, in aqueous solution or in an organic solvent at 25° C. at concentrations which are from 0.1% to 5% depending on the K value range.

Besides the polymeric binders described above, it is possible to employ in particular up to 30% by weight, based on the total weight of the binder, of other binders. Those suitable are polymers, copolymers, cellulose derivatives, starch and starch derivatives, for example:

Polyvinylpyrrolidone (PVP), copolymers of N-vinylpyrrolidone (NVP) and vinyl acetate or vinyl propionate, copolymers of vinyl acetate and crotonic acid, partially hydrolyzed polyvinyl acetate, polyvinyl alcohol, poly(hydroxyalkyl acrylates), poly(hydroxyalkyl methacrylates), polyacrylates and polymethacrylates (Eudragit types), copolymers of methyl methacrylate and acrylic acid, polyacrylamides, polyethylene glycols, polyvinylformamide (partially or completely hydrolyzed where appropriate), cellulose esters, cellulose ethers, especially methyl cellulose and ethyl cellulose, hydroxyalkylcelluloses, especially hydroxypropylcellulose, hydroxyalkylalkylcelluloses, especially hydroxypropylethylcellulose, cellulose phthalates, especially cellulose acetate phthalate and hydroxypropylmethylcellulose phthalate, and mannans, especially galactomannans. Of these, polyvinylpyrrolidone, copolymers of N-vinylpyrrolidone and vinyl esters, poly(hydroxyalkyl acrylates), poly(hydroxyalkyl methacrylates), polyacrylates, polymethacrylates, alkylcelluloses and hydroxyalkylcelluloses are particularly preferred.

The polymeric binder must soften or melt in the complete mixture of all the components in the range of from 50 to 180° C., preferably 60 to 130° C. The glass transition temperature of the mixture must therefore be below 180° C., preferably below 130° C. If necessary, it is reduced by conventional pharmacologically acceptable plasticizing auxiliaries. The amount of plasticizer does not exceed 30% of the total weight of binder and plasticizer in order to form storage-stable drug forms which show no cold flow. However, the mixture preferably contains no plasticizer.

Examples of such plasticizers are:

Long-chain alcohols, ethylene glycol, propylene glycol, glycerol, trimethylolpropane, triethylene glycol, butanediols, pentanols such as pentaerythritol, hexanols, polyethylene glycols, polypropylene glycols, polyethylene/propylene glycols, silicones, aromatic carboxylic esters (e.g. dialkyl phthalates, trimellitic esters, benzoic esters, terephthalic esters) or aliphatic dicarboxylic esters (e.g. dialkyl adipates, sebacic esters, azelaic esters, citric and tartaric esters), fatty acid esters such as glycerol mono-, di- or triacetate or sodium diethyl sulfosuccinate. The concentration of plasticizer is generally from 0.5 to 15, preferably 0.5 to 5,% of the total weight of the mixture.

Conventional pharmaceutical auxiliaries, whose total amount can be up to 100% of the weight of the polymer, are, for example, extenders and bulking agents such as silicates or diatomaceous earth, magnesium oxide, aluminum oxide, titanium oxide, stearic acid or its salts, e.g. the magnesium or calcium salt, methylcellulose, sodium carboxymethylcellulose, talc, sucrose, lactose, cereal or corn starch, potato flour, polyvinyl alcohol, in particular in a concentration of from 0.02 to 50, preferably 0.20 to 20,% of the total weight of the mixture.

Lubricants such as aluminum and calcium stearates, talc and silicones, in a concentration of from 0.1 to 5, preferably 0.1 to 3,% of the total weight of the mixture.

Flowability agents such as animal or vegetable fats, especially in hydrogenated form and those which are solid at room temperature. These fats preferably have a melting point of 50° C. or above. Triglycerides of $C_{12}$, $C_{14}$, $C_{16}$ and $C_{18}$ fatty acids are preferred. It is also possible to use waxes such as carnauba wax. These fats and waxes may be admixed advantageously alone or together with mono- and/or diglycerides or phosphatides, especially lecithin. The mono- and diglycerides are preferably derived from the abovementioned fatty acid types. The total amount of fats, waxes, mono-, diglycerides and/or lecithins is from 0.1 to 30, preferably 0.1 to 5,% of the total weight of the composition for each layer.

Dyes, such as azo dyes, organic or inorganic pigments or dyes of natural origin, with preference for inorganic pigments in a concentration of from 0.001 to 10, preferably 0.5 to 3,% of the total weight of the mixture.

Stabilizers such as antioxidants, light stabilizers, hydroperoxide destroyers, radical scavengers, stabilizers against microbial attack.

It is also possible to add wetting agents, preservatives, disintegrants, adsorbents, release agents and propellants (cf., for example, H. Sucker et al., Pharmazeutische Technologie, Thieme-Verlag, Stuttgart 1978).

Auxiliaries also include for the purpose of the invention substances for producing a solid solution of the active ingredient. Examples of these auxiliaries are pentaerythritol and pentaerythritol tetraacetate, polymers such as polyethylene oxides and polypropylene oxides and their block copolymers (poloxamers), phosphatides such as lecithin, homo- and copolymers of vinylpyrrolidone, surfactants such as polyoxyethylene 40 stearate, and citric and succinic acids, bile acids, sterols and others as indicated, for example, in J. L. Ford, Pharm. Acta Helv. 61 (1986) 69–88.

Auxiliaries are also regarded as being bases and acids added to control the solubility of an active ingredient (see, for example, K. Thoma et al., Pharm. Ind. 51 (1989) 98–101).

The only precondition for the suitability of auxiliaries is adequate thermal stability.

Active ingredients mean for the purpose of the invention all substances with a physiological effect as long as they do not decompose under the processing conditions. These are, in particular, pharmaceutical active ingredients (for humans and animals), active ingredients for plant treatment, insecticides, active ingredients of human and animal foods, fragrances and perfume oils. The amount of active ingredient per dose unit and the concentration may vary within wide limits depending on the activity and the release rate. The only condition is that they suffice to achieve the desired effect. Thus, the concentration of active ingredient can be in the range from 0.1 to 95, preferably from 20 to 80, in particular 30 to 70,% by weight. It is also possible to employ combinations of active ingredients. Active ingredients for the purpose of the invention also include vitamins and minerals. The vitamins include the vitamins of the A group, the B group, by which are meant besides $B_1$, $B_2$, $B_6$ and $B_{12}$ and nicotinic acid and nicotinamide also compounds with vitamin B properties such as adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include therapeutic peptides. Plant treatment agents include, for example, vinclozolin, epoxiconazole and quinmerac.

The novel process is suitable, for example, for processing the following active ingredients:

acebutolol, acetylcysteine, acetylsalicylic acid, aciclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazoline, cefixime, cefotaxime, ceftazidime, ceftriaxone, cefuroxime, selegiline, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures or combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, pentoxifylline, phenoxymethylpenicillin, phenylephrine, phenylpropanolamine, phenytoin, piroxicam, polymyxin B, povidone-iodine, pravastatin, prazepam, prazosin, prednisolone, prednisone, bromocriptine, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproic acid, vancomycin, verapamil, vitamin E, folinic acid, zidovudine.

Preferred active ingredients are ibuprofen (as racemate, enantiomer or enriched enantiomer), ketoprofen, flurbiprofen, acetylsalicylic acid, verapamil, paracetamol, nifedipine or captopril.

To produce the solid dosage forms, a plastic mixture of the components (melt) is prepared and then subjected to a shaping step. There are various ways of mixing the components and forming the melt. The mixing can take place before, during and/or after the formation of the melt. For example, the components can be mixed first and then melted or be mixed and melted simultaneously. The plastic mixture is often then homogenized in order to disperse the active ingredient thoroughly.

However, it has proven preferable, especially when sensitive active ingredients are used, first to melt the polymeric binder and, where appropriate, make a premix with conventional pharmaceutical additives, and then to mix in (homogenize) the sensitive active ingredient(s) in the plastic phase in intensive mixers with very short residence times. The active ingredient(s) can for this purpose be employed in solid form or in solution or dispersion.

The components are generally employed as such in the production process. However, they can also be used in liquid form, i.e. as solution, suspension or dispersion.

Suitable solvents for the liquid form of the components are primarily water or a water-miscible organic solvent or a mixture thereof with water. However, it is also possible to use organic solvents which are immiscible or miscible with water. Suitable water-miscible solvents are, in particular, $C_1$–$C_4$-alkanols such as ethanol, isopropanol or n-propanol, polyols such as ethylene glycol, glycerol and polyethylene glycols. Suitable water-immiscible solvents are alkanes such as pentane or hexane, esters such as ethyl acetate or butyl acetate, chlorinated hydrocarbons such as methylene chloride, and aromatic hydrocarbons such as toluene and xylene. Another solvent which can be used is liquid $CO_2$.

The solvent used in the individual case depends on the component to be taken up and the properties thereof. For example, pharmaceutical active ingredients are frequently used in the form of a salt which is, in general, soluble in water. Water-soluble active ingredients can therefore be employed as aqueous solution or, preferably, be taken up in the aqueous solution or dispersion of the binder. A corresponding statement applies to active ingredients which are soluble in one of the solvents mentioned, if the liquid form of the components used is based on an organic solvent.

It is possible where appropriate to replace melting by dissolving, suspending, or dispersing in the abovementioned solvents, if desired and/or necessary with the addition of suitable auxiliaries such as emulsifiers. The solvent is then generally removed to form the melt in a suitable apparatus, e.g. an extruder. This will be comprised by the term mixing hereinafter.

The melting and/or mixing takes place in an apparatus customary for this purpose. Particularly suitable ones are extruders or containers which can be heated where appropriate and have an agitator, e.g. kneaders (like those of the type to be mentioned below).

A particularly suitable mixing apparatus is one employed for mixing in plastics technology. Suitable apparatuses are described, for example, in "Mischen beim Herstellen und Verarbeiten von Kunststoffen", H. Pahl, VDI-Verlag, 1986. Particularly suitable mixing apparatuses are extruders and dynamic and static mixers, and stirred vessels, single-shaft stirrers with stripper mechanisms, especially paste mixers, multishaft stirrers, especially PDSM mixers, solids mixers and, preferably, mixer/kneader reactors (e.g. ORP, CRP, AP, DTB supplied by List or Reactotherm supplied by Krauss-Maffei or Ko-Kneter supplied by Buss), trough mixers and internal mixers or rotor/stator systems (e.g. Dispax supplied by IKA).

In the case of sensitive active ingredients it is preferable first for the polymeric binder to be melted in an extruder and then for the active ingredient to be admixed in a mixer/kneader reactor. On the other hand, with less sensitive active ingredients, a rotor/stator system can be employed for vigorously dispersing the active ingredient.

The mixing apparatus is charged continuously or batchwise, depending on its design, in a conventional way. Powdered components can be introduced in a free feed, e.g. via a weigh feeder. Plastic compositions can be fed in directly from an extruder or via a gear pump, which is particularly advantageous if the viscosities and pressures are high. Liquid media can be metered in by a suitable pump unit.

The mixture obtained by mixing and/or melting the binder, the active ingredient and, where appropriate, the additive(s) ranges from pasty to viscous (plastic) or fluid and is therefore extrudable. The glass transition temperature of the mixture is below the decomposition temperature of all the components present in the mixture. The binder should preferably be soluble or swellable in a physiological medium.

The steps of mixing and melting in the process can be carried out in the same apparatus or in two or more separately operating apparatuses. The preparation of a premix can take place in one of the conventional mixing apparatuses described above. A premix of this type can then be fed directly, for example, into an extruder and subsequently extruded, where appropriate with the addition of other components.

It is possible in the novel process to employ as extruders single screw machines, intermeshing screw machines or else multiscrew extruders, especially twin screw extruders, corotating or counterrotating and, where appropriate, equipped with kneading disks. If it is necessary in the extrusion to evaporate a solvent, the extruders are generally equipped with an evaporating section. Particularly preferred extruders are those of the ZKS series from Werner & Pfleiderer.

It is also possible according to the invention to produce multilayer pharmaceutical forms by coextrusion, in which case a plurality of mixtures of the components described above is fed together to an extrusion die so as to result in the required layered structure of the multilayer pharmaceutical form. It is preferable to use different binders for different layers.

Multilayer drug forms preferably comprise two or three layers. They may be in open or closed form, in particular as open or closed multilayer tablets.

At least one of the layers contains at least one pharmaceutical active ingredient. It is also possible for another active ingredient to be present in another layer. This has the advantage that two mutually incompatible active ingredients can be processed or that the release characteristics of the active ingredient can be controlled.

The shaping takes place by coextrusion with the mixtures from the individual extruders or other units being fed into a common coextrusion die and extruded. The shape of the coextrusion die depends on the required pharmaceutical form. Examples of suitable dies are those with a flat orifice, called slit dies, and dies with an annular orifice. The design of the die depends on the polymeric binder used and the required pharmaceutical form.

The resulting mixture is preferably solvent-free, i.e. it contains neither water nor an organic solvent.

The plastic mixture is, as a rule, subjected to final shaping. This can result in a large number of shapes depending on the die and mode of shaping. For example, if an extruder is used, the extrudate can be shaped between a belt and a roll, between two belts or between two rolls, as described in EP-A-358 105, or by calendering in a calender with two molding rolls, see, for example, EP-A-240 904. Other shapes can be obtained by extrusion and hot- or cold-cut of the extrudate, for example small-particle and uniformly shaped pellets. Hot-cut pelletization usually results in lenticular dosage forms (tablets) with a diameter of from 1 to 10 mm, while strip pelletization normally results in cylindrical products with a length to diameter ratio of from 1 to 10 and a diameter of from 0.5 to 10 mm. It is thus possible to produce monolayer but also, on use of coextrusion, open or closed multilayer dosage forms, for example oblong tablets, coated tablets, pastilles and pellets. The resulting granules can also be ground to a powder and compressed to tablets in a conventional way. Micropastilles can be produced by the Rotoform-Sandvik process. These dosage forms can be rounded and/or provided with a coating by conventional methods in a subsequent process step. Examples of materials suitable for film coatings are polyacrylates such as the Eudragit types, cellulose esters such as the hydroxypropylcellulose phthalates, and cellulose ethers, such as ethylcellulose, hydroxypropylmethylcellulose or hydroxypropylcellulose.

In specific cases there may be formation of solid solutions. The term solid solutions is familiar to the skilled worker, for example from the literature cited at the outset. In solid solutions of active ingredients in polymers, the active ingredient is in the form of a molecular dispersion in the polymer.

The following examples are intended to illustrate the novel process, without restricting it, however.

EXAMPLES

Example 1

520 g of copolymer of 90% by weight vinylpyrrolidone and 10% by weight stearyl methacrylate (K value 35; 1% strength in water) are extruded and calendered with 480 g of verapamil hydrochloride to give 500 mg oblong tablets under the conditions indicated below.

| | |
|---|---|
| Section 1 | 48° C. |
| Section 2 | 88° C. |
| Section 3 | 131° C. |
| Section 4 | 112° C. |
| Section 5 | 109° C. |
| Die | 100° C. |

Release of the active ingredient from the tablets was investigated by the USP paddle method (pH change). It was 55% after 8 hours.

Example 2

500 g of copolymer of 90% by weight vinylpyrrolidone and 10% by eight stearyl methacrylate (K value 35; 1% strength in water) are extruded with 500 g of vinclozolin under the following conditions, and are cooled and granulated.

| | |
|---|---|
| Section 1 | 60° C. |
| Section 2 | 98° C. |
| Section 3 | 110° C. |
| Section 4 | 115° C. |
| Section 5 | 112° C. |
| Die | 100° C. |

Transparent, X-ray-amorphous, water-dispersible granules were obtained.

We claim:

1. A process for producing solid pharmaceutical, sustained release dosage forms by mixing at least one polymeric binder, at least one pharmaceutical active ingredient and, where appropriate, conventional additives to form a plastic mixture, and shaping, wherein the polymeric binder used is a copolymer of an N-vinyllactam of formula I:

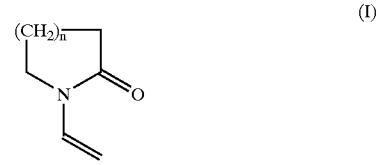

where n is 1, 2 or 3, and 1 to 30 mol % of a monomer having a hydrophobic radical and copolymerizable with the N-vinyllactam, which monomer is selected from the group consisting of compounds of formula II:

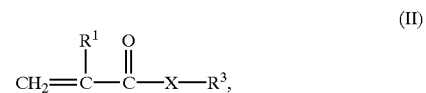

where
$R^1$ is a hydrogen atom or a methyl group;
X is O, NH or $NR^2$, wherein $R^2$ is $C_1$–$C_{30}$-alkyl, and
$R^3$ is $C_8$–$C_{30}$-alkyl, $C_8$–$C_{30}$-cycloalkyl or $C_8$–$C_{30}$-alkenyl, vinyl esters of aliphatic $C_8$–$C_{30}$-carboxylic acids, and mixtures thereof.

2. A process as claimed in claim 1, wherein a copolymer comprising N-vinylpyrrolidone units is used.

3. A process as claimed in claim 1, wherein the copolymer comprises units of a compound of the formula II where $XR^3$ is $OC_8$–$C_{18}$-alkyl, $NHC_8$–$C_{18}$-alkyl or $N(C_8$–$C_{18}$-alkyl$)_2$.

4. A process as claimed in claim 1, wherein the copolymer comprises units of a monomer which is selected from ethylhexyl, lauryl, myristyl, cetyl, stearyl, oleyl or behenyl acrylate or methacrylate as compound of the formula II.

5. A process as claimed in claim 1, wherein the copolymer comprises 50–99% by weight of N-vinyllactam units.

6. A process as claimed in claim 1, wherein the copolymer additionally comprises units of other monomers which are selected from $\alpha,\beta$-ethylenically unsaturated $C_3$–$C_8$-mono- and dicarboxylic acids, their anhydrides, diesters and monoesters with $C_1$–$C_4$-alkanols, $C_1$–$C_4$-diols or di-($C_1$–$C_4$)-alkylamino-$C_1$–$C_4$-alkan-ols, the amides and nitriles of these carboxylic acids, vinyl esters of aliphatic $C_1$–$C_4$-carboxylic acids and the salts or quaternized products thereof.

7. A process as claimed in claim 1, wherein the formation of the plastic mixture takes place by mixing and/or melting the components in an extruder.

8. A process as claimed in claim 1 for producing pharmaceutical dosage forms, plant treatment compositions, animal feed additives and supplements and human food supplements.

9. A solid dosage form obtainable by a process as claimed in claim 1.

10. A process for producing solid pharmaceutical, sustained release dosage forms by mixing at least one polymeric binder, at least one pharmaceutical active ingredient and, where appropriate, conventional additives to form a plastic mixture, and shaping, wherein the polymeric binder used is a copolymer of an N-vinyllactam of formula I:

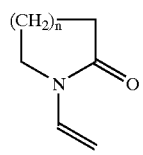
(I)

where n is 1, 2 or 3, and 1 to 30 mol % of a monomer having a hydrophobic radical and copolymerizable with the N-vinyllactam, which monomer is selected from the group consisting of compounds of formula II:

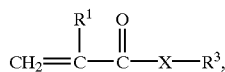
(II)

where
$R^1$ is a hydrogen atom or a methyl group;
X is O, NH or $NR^2$, wherein $R^2$ is $C_1$–$C_{30}$-alkyl, and
$R^3$ is $C_8$–$C_{30}$-alkyl, $C_8$–$C_{30}$-cycloalkyl or $C_8$–$C_{30}$-alkenyl, vinyl esters of aliphatic $C_8$–$C_{30}$-carboxylic acids, and mixtures thereof, wherein the copolymer comprises 70–99% by weight of N-vinyllactam units.

11. A solid dosage form obtainable by the process of claim 8.

12. A solid dosage form comprising
a) from 10 to 99.9% by weight of one or more polymeric binders,
b) from 0.1 to 90% by weight of one or more active ingredients selected from the group of pharmaceutical active ingredients, plant treatment active ingredients, animal feed additives and supplements and human food supplements,
the sum of (a) and (b) being 100 percent by weight, and optionally conventional additives, wherein (a) consists essentially of one or more copolymers of
i) an N-vinyllactam of formula I

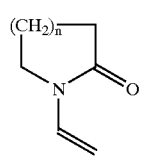
(I)

wherein n is 1, 2 or 3, and
ii) from 1 to 30 mol % of at least one monomer having a hydrophobic radical which is copolymerizable with the N-vinyllactam and being selected from the group consisting of a vinyl ester of an aliphatic $C_8$–$C_{30}$-carboxylic acid and a compound of formula II:

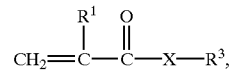
(II)

wherein
$R^1$ is a hydrogen or methyl;
X is O, NH or $NR^2$,
$R^2$ is $C_1$–$C_{30}$-alkyl, and
$R^3$ is $C_8$–$C_{30}$-alkyl, $C_8$–$C_{30}$-cycloalkyl or $C_8$–$C_{30}$-alkenyl.

13. The dosage form defined in claim 12, wherein (b) consists of one or more pharmaceutical active ingredients.

14. The dosage form defined in claim 12, wherein (a) consists of
$a_1$) from 70 to 100% by weight of the one or more N-vinyllactam copolymers, and
$a_2$) from 0 to 30% by weight of one or more polymeric binders different from ($a_1$).

15. The dosage form defined in claim 12, wherein the N-vinyllactam copolymer comprises N-vinylpyrrolidone units.

16. The dosage form defined in claim 12, wherein the N-vinyllactam copolymer comprises units of the compound of formula II wherein $XR^3$ is $OC_8$–$C_{18}$-alkyl, $NHC_8$–$C_{18}$-alkyl or $N(C_8$–$C_{18}$-alkyl$)_2$.

17. The dosage form defined in claim 12, wherein the N-vinyllactam copolymer comprises units of the compound of formula II wherein $R^1$ is hydrogen or methyl, X is oxygen and $R^3$ is ethylhexyl, lauryl, myristyl, cetyl, stearyl, oleyl or behenyl.

18. The dosage form defined in claim 12, wherein the N-vinyllactam copolymer comprises 50–99% by weight of N-vinyllactam units.

19. The dosage form defined in claim 12, wherein the N-vinyllactam copolymer comprises 70–99% by weight of N-vinyllactam units.

20. The dosage form defined in claim 12, wherein the N-vinyllactam copolymer further comprises units of one or more monomers selected from the group consisting of α,β-ethylenically unsaturated $C_3$–$C_8$-mono- and dicarboxylic acids, their anhydrides, and their diesters and monoesters with $C_1$–$C_4$-alkanols, $C_1$–$C_4$-diols and di-($C_1$–$C_4$)-alkylamino-$C_1$–$C_4$-alkanols, their amides and their nitriles, vinyl esters of aliphatic $C_1$–$C_4$-carboxylic acids and the salts or quaternized products thereof.

* * * * *